United States Patent [19]

Hannula et al.

[11] Patent Number: 4,776,791

[45] Date of Patent: Oct. 11, 1988

[54] SHIELD FOR A PAIR OF ORTHODONTIC PLIERS FOR USE IN REMOVING DENTAL BRACKETS

[75] Inventors: Donald L. Hannula, San Diego; Frank Silva, Cardiff, both of Calif.

[73] Assignee: Johnson & Johnson Consumer Products, Inc., Brunswick, N.J.

[21] Appl. No.: 142,988

[22] Filed: Jan. 12, 1988

[51] Int. Cl.[4] ................................................ A61C 7/00
[52] U.S. Cl. ....................................................... 433/4
[58] Field of Search ..................................... 433/159, 4

[56] References Cited

U.S. PATENT DOCUMENTS 3,755,902 9/1973 Northcutt ................................ 433/4
3,986,265 10/1976 Cusato ..................................... 433/4

Primary Examiner—Robert Peshock
Attorney, Agent, or Firm—Donal B. Tobin

[57] ABSTRACT

A shield for use with a pair of orthodontic pliers in removing an orthodontic bracket. The shield fits snuggly onto one jaw of the pliers and provides side walls adjacent the plier jaws. The jaws have a recess near their distal end such that the confronting surfaces of the jaw recesses and the confronting surfaces of the side walls provide an enclosure about a bracket while it is being removed so that if it fractures the enclosure will contain any pieces that may break off the bracket.

11 Claims, 3 Drawing Sheets

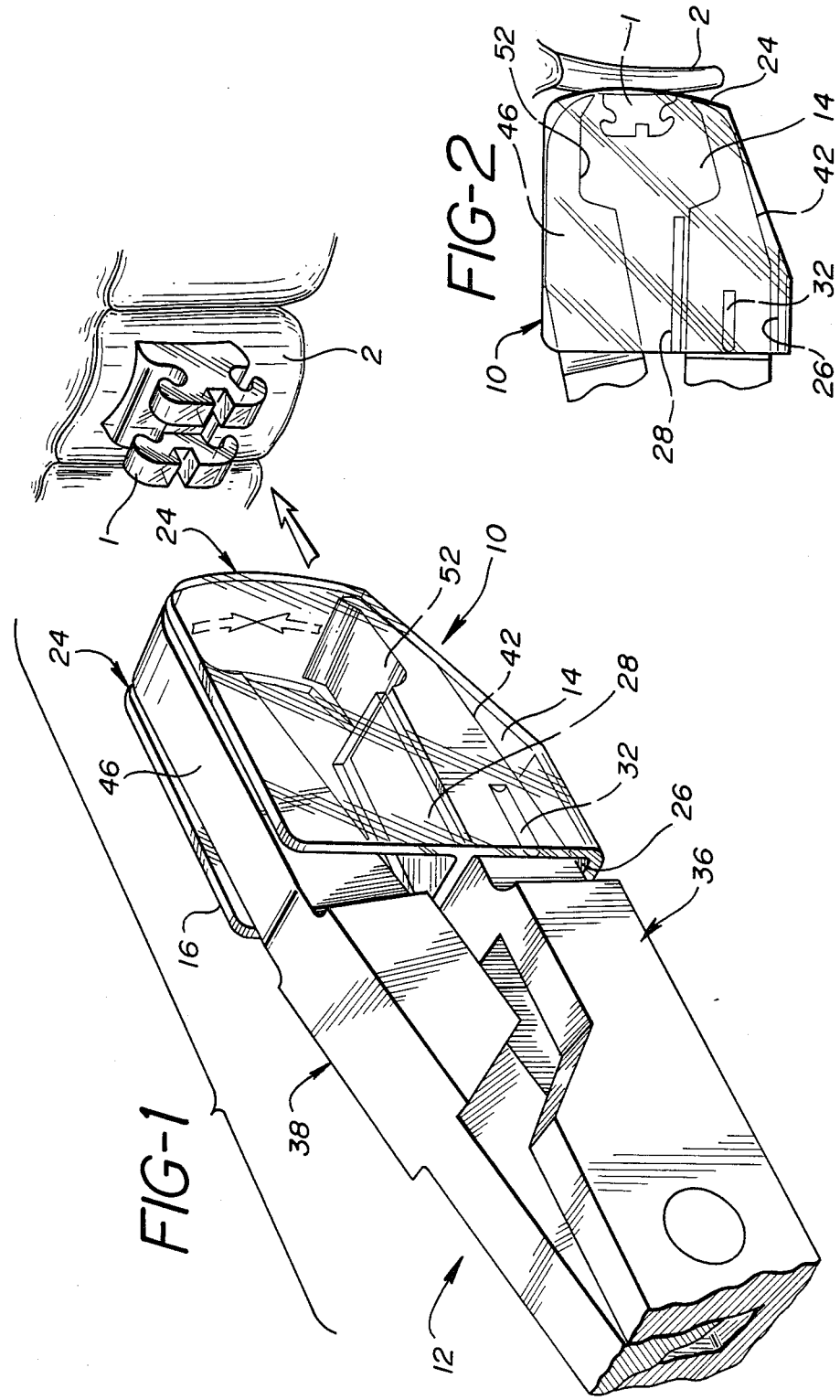

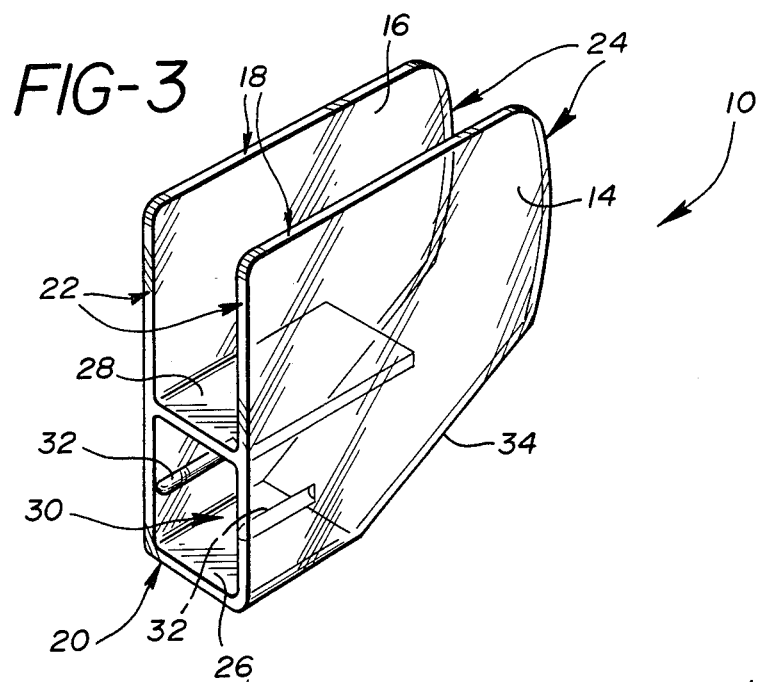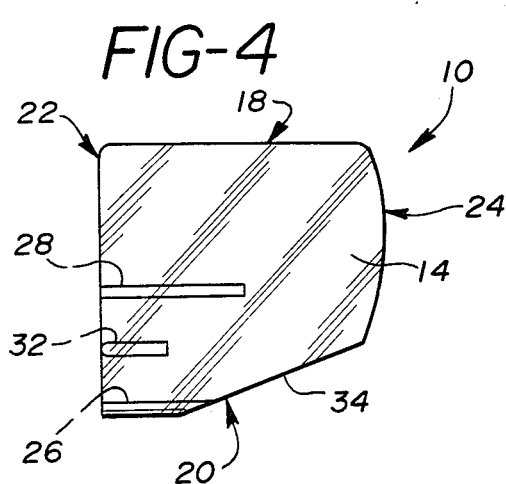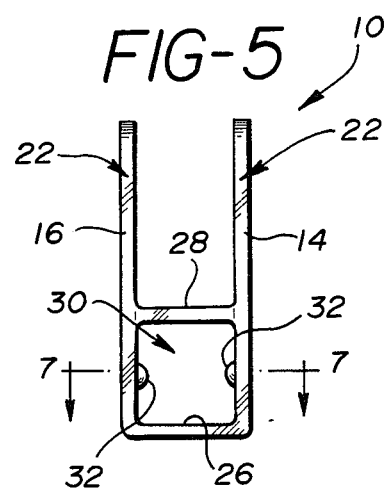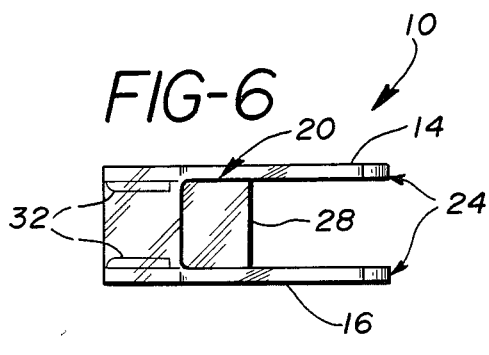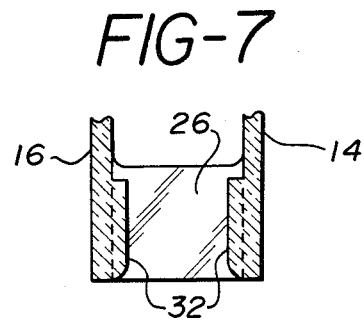

SHIELD FOR A PAIR OF ORTHODONTIC PLIERS FOR USE IN REMOVING DENTAL BRACKETS

The present invention relates to a shield for orthodontic pliers used to remove orthodontic brackets from a tooth and, more particularly, to a shield which will provide an enclosure to contain pieces that may break off the bracket during removal.

BACKGROUND OF THE INVENTION

Orthodontic brackets attach directly to the teeth and serve to transmit corrective forces from an orthodontic arch wire to the tooth to which the bracket is attached. When the orthodontic procedure is complete or from time to time during the course of an orthodontic regimen it may be necessary to remove the bracket from the teeth. In the past, orthodontic brackets have been made of metal material so that they could be removed with an ordinary pair of pliers. Recent developments in orthodonture have provided transparent orthodontic brackets made of brittle material such as crystalline alumina. This new kind of bracket is described in U.S. Pat. No. 4,639,218 issued Jan. 29, 1987. These new kinds of transparent crystalline orthodontic brackets are often brittle so that when they are subjected to the forces necessary to remove them from the teeth to which they are attached, they might shatter.

It would be desirable to have a shield to be used with an orthodontic pliers to enclose the bracket during removal so that any pieces which may break from the bracket will be contained.

SUMMARY OF THE INVENTION

The present invention provides a shield for a pair of pliers for use in removing an orthodontic bracket from a tooth. The shield includes first and second side walls spaced apart a distance about equal to the width of the pliers. Each of the side walls has a top, bottom, front and back edge. The terms top, bottom, front and back are not intended to designate orientation but are merely a convenient way of designating specific parts of the shield. When the shield is in a pair of pliers, the front is meant to indicate the part nearest the tips of the jaws of the pliers. The back part of the shield side walls is meant to indicate that part closest to the pivot point of the pliers. The top and bottom are used to indicate the other edges of each side wall. In use, the shield can be oriented in any way that is convenient to the user and the part designated as top in this application could very well be oriented so as to appear as the bottom and vice versa.

First and second webs connect at least portions of the first and second side walls and are spaced from each other to define a channel for receiving one jaw of the pliers. The second web is aligned between the pliers jaws when the pliers is closed. A rib may be placed on the interior of the channel to provide a snug fit with the confronting surface of the jaw of the pliers. The ribs may be on any opposing surfaces of the channel.

The bottom edge of each side wall may be beveled in a direction toward the front edge of each side wall. The front edge of each side wall may be curved to follow the arc of motion of the pliers jaws.

The first and second webs may be parallel and the first web may be aligned with the bottom edges of the first and second side walls. The second web may extend in a direction perpendicular to the back edges of each side wall a distance about half way to the front edge of each side wall. The distance between the side walls is greater than the width of the bracket which is intended to be removed.

Each jaw of the pliers has a sharp distal end in the recess extending away from the sharp distal end of each jaw. When the pliers are inserted in the shield and grasp a bracket for removal, the confronting surfaces of the jaw recess and the side walls of the shield provide an enclosure about the bracket for containing any pieces that may break from the bracket during removal.

The distal tip of each jaw may include a concave recess to better fit against the tooth.

These and other features and advantages of the present invention will become more apparent from the following detailed description of the preferred embodiments taken in conjunction with the following drawings.

BRIEF DESCRIPTION OF THE DRAWINGS

FIG. 1 shows a perspective view of the present invention in its relationship to a bracket affixed to a tooth;

FIG. 2 shows a side elevational view of the shield of the present invention with the jaws of the pliers in place about an orthodontic bracket to be removed;

FIG. 3 shows a perspective view of the shield;

FIG. 4 shows a side elevational view of the shield;

FIG. 5 shows a rear elevational view of the shield;

FIG. 6 shows a bottom plan view of the shield;

FIG. 7 shows a sectional view of a portion of the shield taken along lines 7—7 in FIG. 5;

DETAILED DESCRIPTION OF THE PREFERRED EMBODIMENT

Figure 8:
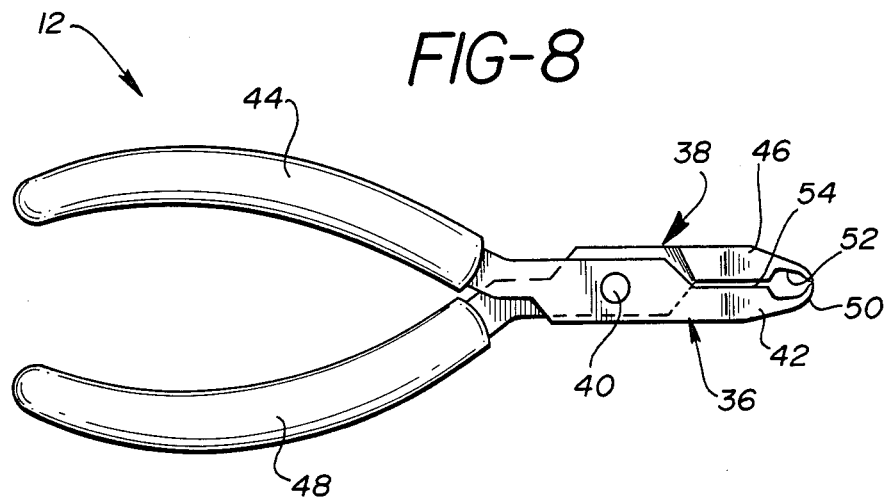
FIG. 8 shows a plan view of the pliers.

Referring now to FIG. 1 there is shown a orthodontic bracket 1 of the kind described in U.S. Pat. No. 4,639,218 mounted on a tooth 2 with shield 10 mounted on pliers 12 in a position to grasp bracket 1.

Referring now to FIGS. 3 through 7, it can be seen that shield 10 has first and second side walls 14 and 16 spaced apart a predetermined distance. Each side wall has a top edge, bottom edge, back edge and front edge 18, 20, 22 and 24, respectively. A first web 26 connects at least a portion of bottom edges 20 of side walls 14 and 16. A second web 28 spaced apart from and generally parallel to the first web 26 also connects first and second side walls 14 and 16 and extends generally perpendicular to back edges 22 of side walls 14 and 16 in a direction toward the front edge 24 of each side wall 14 and 16 and extends a distance about half way from back edges 22 toward front edges 24. The confronting surfaces of first web 26, second web 28, first side wall 14 and second side wall 16 define a channel 30 for receiving one jaw of pliers 12.

Ribs 32 on the inside surfaces of side walls 14 and 16 project into channel 30 to provide a means for tightly fitting to the opposite sides of the jaw of pliers 12 to provide a snug fit between shield 10 and pliers 12.

Bottom edge 20 of each of side walls 14 and 16 includes a bevel portion 34 extending from first web 26 toward front edge 24. Bevel portion 34 is preferably disposed at about a 20° angle to the plane of first web 26 but this angle is not critical and any convenient angle may be used.

Front edge 24 of each of side walls 14 and 16 is curved on a convex arc which conforms to the arc of motion of the tip of the jaw of pliers 12. The purpose of using bevel 34 is to remove excess material from the shield to provide more convenient access to the orthodontic bracket, better visibility for the user and cosmetic appearance of the shield. The purpose of using the curvage pn frong edge 24 is to maximize the coverage of the tips without having the shield protrude beyond the tips. The curve of the shield follows the arc of motion of the plier jaws.

Referring now to FIGS. 8 through 11 there is shown a pliers 12 that may be used with shield 10. pliers 12 has a first and second member 36 and 38 respectively that pivot together at point 40. Member 36 has a jaw 42 at its distal end and a handle 44 at its proximal end. Member 38 has a jaw 46 at its distal end and a handle 48 at its proximal end.

Figure 9:
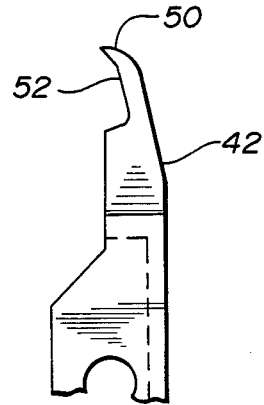
FIG. 9 shows a side elevational view of one jaw of the pliers.
Figure 10:
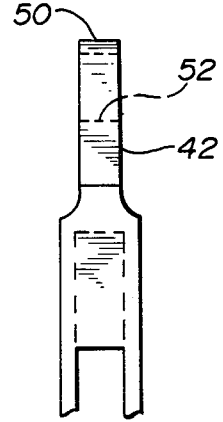
FIG. 10 shows a bottom plan view of one jaw of the pliers.

Referring now to FIG. 9 there is shown jaw 42 of member 38. The distal end 50 of each member 36 and 38 is sharpened to a relatively sharp edge. A recess 52 extends proximally from sharpened distal end 50 and extends transversely completely across each jaw 42 and 46.

In operation, it can be seen particularly from FIG. 2 that jaw 42 of member 36 may be inserted within channel 30 of shield 10 and jaw 46 of member 38 is free to rotate within the space provided between side walls 14 and 16 above second web 28. The arcuate front edge 24 of side walls 14 and 16 conforms to the arc of rotation of the distal end 50 of jaws 42 and 46. It can be seen from FIG. 8 that a small gap 54 exists between jaws 42 and 46 when they are closed together. Referring again to FIG. 2, it can be seen that gap 54 leaves room for second web 28 to be confined in gap 54 between jaws 42 and 46 when the jaws are closed. This gap permits the jaws to completely closed without cutting or damaging web 28.

Referring again to FIG. 2, the user places the distal tips 50 of jaws 42 and 46 adjacent tooth 2 and about bracket 1. The transverse distance across the jaws is greater than the transverse dimension of bracket 1. The side walls 14 and 16 of shield 10 fits snuggly against the sides of jaws 42 and 46 to completely enclose the portion of bracket 1 that projects from the tooth. Thus, it can be seen that as the jaws are closed to tightly grip the bracket 1 and the pliers is manipulated or squeezed to loosen bracket 1 from tooth 2, bracket 1 is completely enclosed by the confronting surfaces of recesses 52 in jaws 42 and 46 and side walls 14 and 16. Thus, if any part of bracket 1 breaks off during removal, it will be contained within the space provided between the confronting surfaces of jaws 42 and 46 and side walls 14 and 16 of shield 10.

Figure 12:
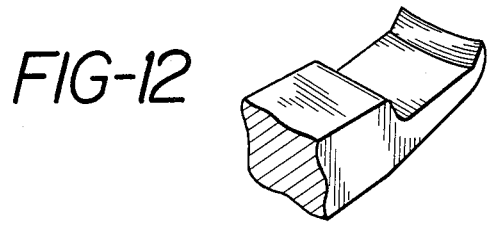
FIG. 12 shows an alternative concave jaw tip.
Figure 11:
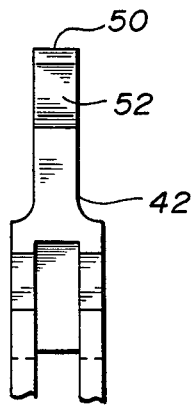
FIG. 11 shows a top plan view of one jaw of the pliers.

Referring now to FIG. 12, there is shown a modified jaw tip 51 for jaws 42 and 46. Jaw tip 51 includes a concave recess 53 to conform generally to the shape of the interface of bracket 1 and the tooth on which it is used to make removal of bracket 1 easier.

The present invention provides a convenient and effective way of removing orthodontic brackets.

The present invention has been described in conjunction with the preferred embodiments. Those skilled in the art will appreciate that many modifications and changes may be made to the preferred embodiments without departing from the present invention. It is, therefore, not intended to limit the present invention except as set forth in the appended claims.

I claim:

1. A shield for a pair of orthodontic pliers for use in removing an orthodontic bracket from a tooth of a patient comprising:
   first and second qenerally parallel side walls spaced apart a predetermined distance, each side wall havinq a top, bottom, front and back edge;
   a first web connecting at least a portion of said first and second side walls;
   a second web connecting at least a portion of said first and second side walls and spaced from said first web to define a channel for receiving one jaw of a pliers;
   said second web aligned between the pliers jaws when said pliers are closed.

2. The shield of claim 1 further including at least one rib on opposing surfaces of said channel, projecting into said channel to provide a means for holding said shield snuggly on the jaw of a pliers.

3. The shield of claim 1 further including ribs on opposing surfaces of each of said side walls within said channel.

4. The shield of claim 1 wherein the bottom edge of each of said side walls is beveled in a direction running towards said front edge.

5. The shield of claim 1 wherein at least a portion of the front edge of each of said first and second side walls is curved to follow the arc of motion of the pliers jaws.

6. The shield of claim 1 wherein said first and second webs are parallel to each other.

7. The shield of claim 4 wherein said first web extends from the back edge of each of said first and second side walls to a point on said bottom edge of each of said first and second side walls where said bottom edge starts to bevel.

8. The shield of claim 1 wherein said second web extends generally perpendicular to the back edges of said first and second side walls about half way to said front edge of said first and second side walls.

9. The shield of claim 1 wherein the distance between said first and second side walls is greater than the width of a bracket in whose removal said shield is used.

10. The shield of claim 1 further including pliers with first and second members pivotably connected together, each of said members having a handle at its proximal end and a jaw at its distal end;
    each of said jaws having a sharp distal edge and a recess extending proximally from said distal edge;
    one of said jaws disposed in said channel and the other of said jaws being disposed for pivotable movement in the space defined between said second web and the opposing surfaces of said first and second side wall;
    said predetermined distance between said first and second side walls closely conforming to the width of each plier jaw;
    whereby when said pliers jaws are placed on a bracket for removal said sharp distal edges of each jaw, the recess on each of said jaws and said confronting surfaces of said first and seconds side walls combine to form an enclosure about the bracket to confine any pieces that may break off of the bracket during removal.

11. The shield of claim 10 wherein the distal edge of said jaws includes a concave recess to generally conform to the tooth.

* * * * *